(12) United States Patent
Rawson et al.

(10) Patent No.: US 11,950,801 B2
(45) Date of Patent: Apr. 9, 2024

(54) GEARBOX FOR ATHERECTOMY SYSTEM

(71) Applicant: BOSTON SCIENTIFIC SCIMED, INC., Maple Grove, MN (US)

(72) Inventors: Robert Rawson, North Branch, MN (US); Laszlo Trent Farago, Hudson, WI (US); David Gordon Spangler, New Richmond, WI (US); Daniel Frank Massimini, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 603 days.

(21) Appl. No.: 16/746,092

(22) Filed: Jan. 17, 2020

(65) Prior Publication Data

US 2020/0229844 A1    Jul. 23, 2020

Related U.S. Application Data

(60) Provisional application No. 62/794,391, filed on Jan. 18, 2019.

(51) Int. Cl.
*A61B 17/3207*        (2006.01)

(52) U.S. Cl.
CPC .......... *A61B 17/320758* (2013.01); *A61B 2017/320766* (2013.01); *A61B 2017/320775* (2013.01)

(58) Field of Classification Search
CPC .... A61B 17/320758; A61B 17/320725; A61B 17/32075; A61B 17/320783; A61B 17/3207

See application file for complete search history.

(56) References Cited

U.S. PATENT DOCUMENTS

| 5,314,407 | A | 5/1994 | Auth et al. | |
|---|---|---|---|---|
| 10,130,437 | B2* | 11/2018 | Lee | A61B 34/30 |
| 2002/0151917 | A1* | 10/2002 | Barry | A61B 17/320758 |
| | | | | 606/159 |

(Continued)

FOREIGN PATENT DOCUMENTS

| EP | 3132760 A1 | 2/2017 |
|---|---|---|
| EP | 3222228 A1 | 9/2017 |
| WO | 2016144834 A1 | 9/2016 |

OTHER PUBLICATIONS

International Search Report and Written Opinion dated Mar. 30, 2020 for International Application No. PCT/US2020/014062.

*Primary Examiner* — Tuan V Nguyen
(74) *Attorney, Agent, or Firm* — Seager, Tufte & Wickhem, LLP

(57) ABSTRACT

An atherectomy system includes a handle having a handle housing, with a drive member extending through the handle housing and operably coupled to an atherectomy burr. A drive mechanism is disposed within the handle housing and is adapted to rotatably engage the drive member. The drive mechanism may include an electric drive motor, a drive gear that is rotatably engaged with the electric drive motor and a driven gear that is coupled with the drive member and is engaged with the drive gear such that rotation of the driven gear causes rotation of the drive member. The drive mechanism may be configured to enable a rotation speed of the atherectomy burr of up to at least about 200,000 revolutions per minute (rpm).

18 Claims, 9 Drawing Sheets

(56) References Cited

U.S. PATENT DOCUMENTS

| | | | |
|---|---|---|---|
| 2005/0240146 A1* | 10/2005 | Nash | A61M 1/80 |
| | | | 604/35 |
| 2008/0097499 A1* | 4/2008 | Nash | A61B 17/320783 |
| | | | 606/159 |
| 2009/0024085 A1 | 1/2009 | To et al. | |
| 2009/0069829 A1* | 3/2009 | Shturman | A61B 17/3207 |
| | | | 606/159 |
| 2015/0164540 A1 | 6/2015 | Higgins et al. | |
| 2015/0327880 A1* | 11/2015 | Wasicek | A61B 17/32002 |
| | | | 606/115 |
| 2016/0354107 A1 | 12/2016 | Nakano et al. | |
| 2017/0273698 A1* | 9/2017 | McGuckin, Jr. | A61B 17/22 |
| 2021/0172499 A1* | 6/2021 | Nino | B25B 21/00 |

\* cited by examiner

GEARBOX FOR ATHERECTOMY SYSTEM

CROSS-REFERENCE TO RELATED APPLICATIONS

This application claims the benefit of priority under 35 U.S.C. § 119 to U.S. Provisional application Ser. No. 62/794,391, filed Jan. 18, 2019, the entirety of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, the disclosure is directed to an atherectomy system that includes a handle having a handle housing and a drive member that extends through the handle housing and is operably coupled to an atherectomy burr. A drive mechanism is disposed within the handle housing and is adapted to rotatably engage the drive member. The drive mechanism includes an electric drive motor, a drive gear that is rotatably engaged with the electric drive motor and a driven gear that is coupled with the drive member and engaged with the drive gear such that rotation of the driven gear causes rotation of the drive member. The drive mechanism is configured to enable a rotation speed of the atherectomy burr of up to at least about 200,000 revolutions per minute (rpm).

Alternatively or additionally, the drive mechanism may be configured to enable a rotation speed of the atherectomy burr of up to about 250,000 rpm.

Alternatively or additionally, the drive gear and the driven gear may be configured such that the driven gear goes through about 2 to about 5 revolutions per revolution of the drive gear.

Alternatively or additionally, the drive member may be configured to accommodate a guidewire extending through the drive member.

Alternatively or additionally, the atherectomy system may further include a fluid pump built into the drive mechanism.

Alternatively or additionally, the fluid pump may include an impeller that is secured to the drive member such that the impeller rotates with the drive member, and the impeller is in fluid communication with a source of fluid.

Alternatively or additionally, the atherectomy system may further include a shaft seal member that defines a fluid chamber that is in fluid communication with the source of fluid, and the shaft seal member may be configured to permit the drive member to extend therethrough with the impeller disposed within the fluid chamber.

Alternatively or additionally, the atherectomy system may further include an outer tubular member extending distally of the shaft seal member, such that the drive member extends distally through the outer tubular member, defining an annular space through which fluid may be expelled via the impeller.

In another example, the disclosure is directed to an atherectomy system that includes a handle having a handle housing and a drive member that extends through the handle housing and is operably coupled to an atherectomy burr. The atherectomy system includes an electric drive motor, a drive train that operably couples the electric drive motor to the drive member and a fluid pump that is driven by the electric drive motor.

Alternatively or additionally, the drive train may include a drive gear that is rotatably engaged with the electric drive motor and a driven gear that is coupled with the drive member and is engaged with the drive gear such that rotation of the driven gear causes rotation of the drive member.

Alternatively or additionally, the fluid pump may include an impeller that is secured to the drive member such that the impeller rotates with the drive member, and the impeller is in fluid communication with a source of fluid.

Alternatively or additionally, the atherectomy system may further include a fluid chamber that is in fluid communication with the source of fluid, with the impeller disposed within the fluid chamber.

Alternatively or additionally, the drive train may be configured to enable a rotation speed of the atherectomy burr of up to at least about 200,000 revolutions per minute (rpm).

Alternatively or additionally, the fluid pump may provide a fluid pressure of at least about 10 pounds per square inch (psi) to about 100 psi.

In another example, the disclosure is directed to an atherectomy system that includes a handle having a handle housing and a drive member that extends through the handle housing and is operably coupled to an atherectomy burr. A drive mechanism is disposed within the handle housing and is adapted to rotatably engage the drive member. The drive mechanism includes an electric drive motor, a drive gear that is rotatably engaged with the electric drive motor, and a driven gear that is coupled with the drive member and is engaged with the drive gear such that rotation of the driven gear causes rotation of the drive member, wherein the drive mechanism is configured to enable a rotation speed of the atherectomy burr of up to at least about 200,000 revolutions per minute (rpm). A fluid pump is driven by the drive mechanism.

Alternatively or additionally, the fluid pump may include an impeller that is secured to the drive member such that the impeller rotates with the drive member, and the impeller is in fluid communication with a source of fluid.

Alternatively or additionally, the atherectomy system may further include a fluid chamber that is in fluid communication with the source of fluid, with the impeller disposed within the fluid chamber.

Alternatively or additionally, the drive gear may include a polymeric drive gear.

Alternatively or additionally, the driven gear may include a metallic driven gear.

Alternatively or additionally, the drive gear may include a polyetheretherketone (PEEK) drive gear and the driven gear may include an aluminum driven gear.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
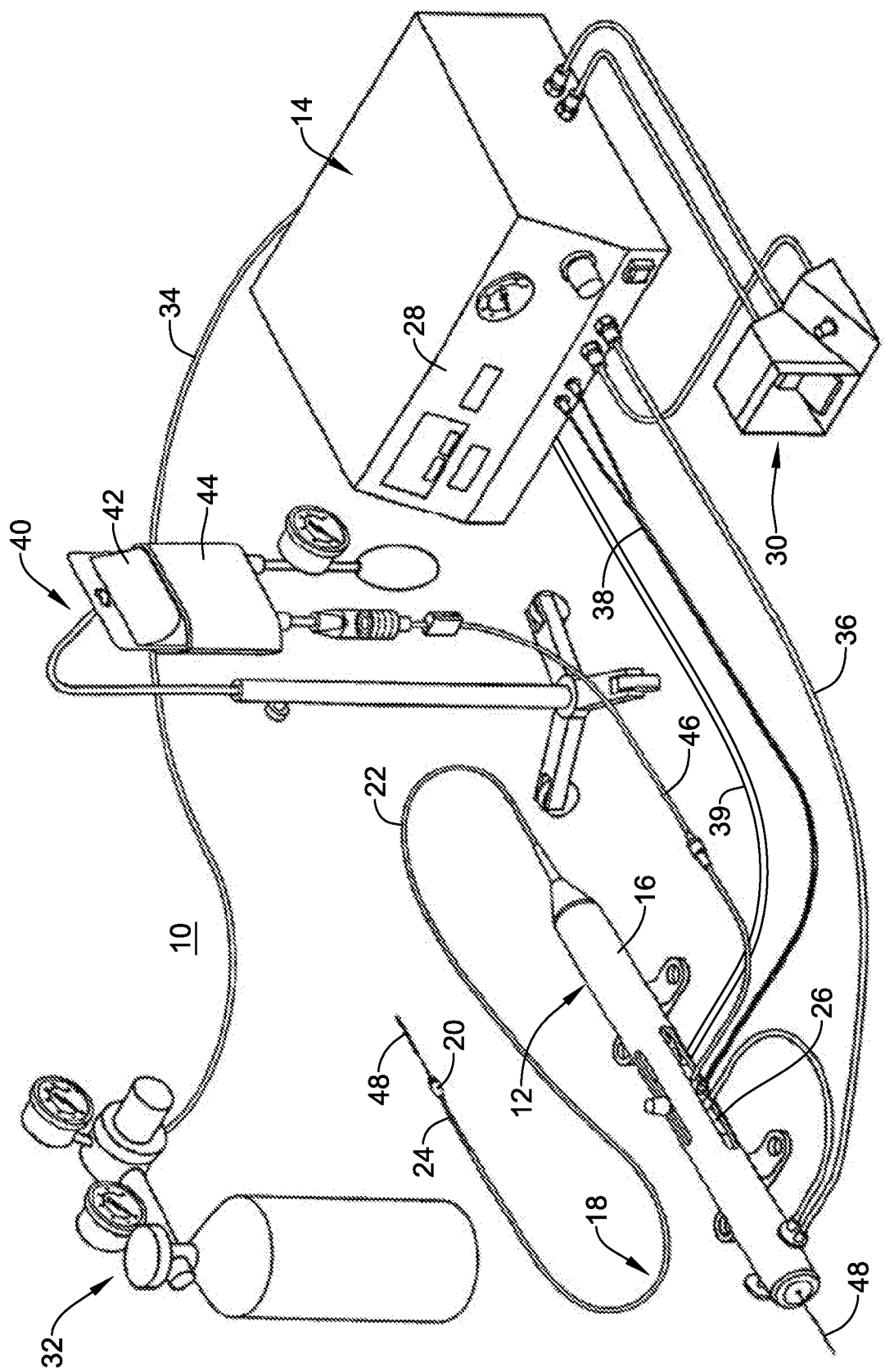
FIG. 1 is a schematic diagram of an illustrative atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

FIG. 1 shows an example rotational atherectomy system 10. The rotational atherectomy system 10 may include a rotational atherectomy device 12 and a controller 14 for controlling the rotational atherectomy device 12. The rotational atherectomy device 12 may include a housing 16 and an elongate shaft 18 extending distally from the housing 16 to a cutting member 20 located at a distal end of the elongate shaft 18. The elongate shaft 18 may include a drive shaft 24 to provide rotational motion to the cutting member 20. In some instances, the elongate shaft 18 may include an outer tubular member 22 having a lumen extending therethrough and the drive shaft 24 may extend through the lumen of the outer tubular member 22. The drive shaft 24, which may be fixed to the cutting member 20, may be rotatable relative to the outer tubular member 22 to rotate the cutting member 20. In some instances the axial position of the cutting member 20 relative to the outer tubular member 22 may be adjusted by moving the drive shaft 24 longitudinally relative to the outer tubular member 22. For example, the atherectomy device 12 may include an advancer assembly 26 positioned in the housing 16, or otherwise provided with the housing 16, that is longitudinally movable relative to the housing 16. The outer tubular member 22 may be coupled to the housing 16 while the drive shaft 24 may be coupled to the advancer assembly 26. Accordingly, the drive shaft 24 (and thus the cutting member 20) may be longitudinally movable relative to the outer tubular member 22 by actuating the advancer assembly 26 relative to the housing 16. In some cases, the advancer assembly 26 may be secured at a particular location within the housing 16, and thus may not be advanceable relative to the housing 16.

The rotational atherectomy device 12 may include a prime mover (not shown) to provide rotational motion to the drive shaft 24 to rotate the cutting member 20. For example, in some instances the prime mover may be a fluid turbine within the housing 16, such as provided with the advancer assembly 26. In other instances, however, the prime mover may be an electrical motor, or the like. The controller 14 may be used to control the prime mover. For example, the user may provide power to the prime mover and/or control the speed of rotation of the drive shaft 24 via the controller 14. For example, the front panel 28 of the controller 14 may include a user interface including a power switch, speed control mechanism (e.g., a speed control knob and/or buttons), a display, and/or other features for controlling the rotational atherectomy device 12. In some instances, the rotational atherectomy system 10 may include a remote control device 30, such as a foot pedal, a hand control, or other mechanism which may be used to control the power and/or speed to the prime mover, for example. In instances in which the prime mover is an electric motor, the electric motor may be coupled to the controller 14 via an electrical connection 39 to control the electric motor and/or provide electricity to the electric motor.

In some instances, the rotational atherectomy device 12 may include a speed sensor, such as an optical speed sensor, coupled to the controller 14 via a connector 38, such as a fiber optic connector to provide speed data to the controller 14. In other instances, an electronic sensor, such as a Hall Effect sensor, or other type of sensor may be used to sense the speed of the drive shaft 24 and cutting member 20. The speed data may be displayed, such as on the front panel 28 and/or the controller 14, and/or used to control the speed of the cutting member 20, such as maintaining a desired speed of the cutting member 20 during a medical procedure.

In some instances, the rotational atherectomy system 10 may be configured to infuse fluid through the elongate shaft 18 to the treatment site and/or aspirate fluid through the elongate shaft 18 from the treatment site. In some cases, the rotational atherectomy system 10 may include a vacuum line 36 for aspiration purposes. For example, the rotational atherectomy system 10 may include a fluid supply 40 for providing a flow of fluid through a lumen of the elongate shaft 18 to a treatment site. In some instances the fluid supply 40 may include a saline bag 42 which may be pressurized by a pressure cuff 44 to provide a pressurized fluid (e.g., saline) to the rotational atherectomy device 12 through a fluid supply line 46. In other instances, an infusion pump, such as a peristaltic pump, may be used to deliver pressurized fluid to the rotational atherectomy device 12. Additionally or alternatively, in some cases the rotational atherectomy system 10 may be configured to aspirate fluid from the treatment site. For example, the rotational atherectomy system 10 may include an aspiration pump, such as a peristaltic pump, to generate a vacuum to aspirate fluid through a lumen of the elongate shaft 18 to a fluid collection container (not shown), if desired. In some instances, the elongate shaft 18 of the rotational atherectomy device 12 may be advanced over a guidewire 48 to a treatment site. For example, the drive shaft 24 may include a guidewire lumen through which the guidewire 48 may pass. Additionally or alternatively, the elongate shaft 18 may be advanced through a lumen of a guide catheter to a treatment site.

Figure 2:
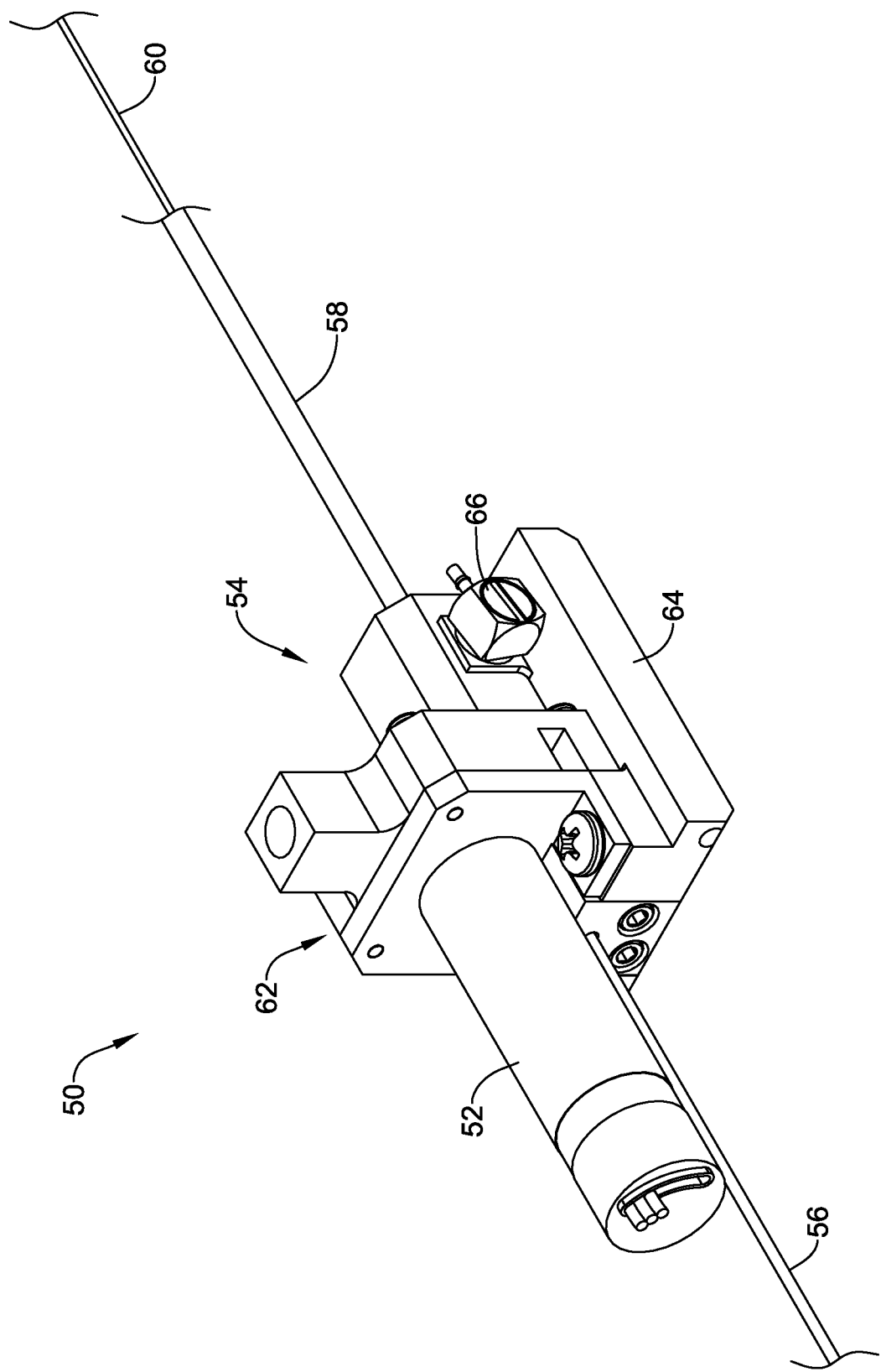
FIG. 2 is a perspective view of an illustrative drive mechanism forming a portion of the illustrative atherectomy system of FIG. 1.

As noted, in some cases the prime mover may be an electric motor. FIG. 2 is a perspective view of a drive mechanism 50 that may be used in the rotational atherectomy system 10. The drive mechanism 50 includes an electric drive motor 52 that is secured relative to a housing 54. A proximal tubular member 56 extends proximally from the housing 54 and may be considered as being configured to accommodate a guidewire such as the guidewire 48 shown in FIG. 1. A distal tubular member 58 extends distally from the housing 54. A drive member 60 may be seen as extending distally from within the distal tubular member 58. While not expressly shown, it will be appreciated that the drive member 60 may define a lumen extending therethrough in order to accommodate the aforementioned guidewire.

In some cases, the housing 54 may be considered as including a drive gear housing 62 that serves to house and protect a drive gear (as will be shown) that is operably coupled to an output shaft of the electric drive motor 52. The housing 54 may be considered as including a lower housing portion 64 that serves to house and protect a driven gear (as will be shown) that is operably coupled to the drive member 60 such that rotation of the driven gear (via the drive gear) causes rotation of the drive member 60. It will be appreciated that a distal portion of the drive member 60 may be operably coupled to the drive shaft 24 (FIG. 1). In some cases, the distal portion of the drive member 60 may form the drive shaft 24. The lower housing portion 64 includes a fitting 66 that is in fluid communication with a fluid pump (not visible in FIG. 2) that is disposed within the lower housing portion 64 and that is configured to provide pressurized fluid such as saline through the distal tubular member 58. While not illustrated, it will be appreciated that the distal tubular member 58 may accommodate one or more additional tubular members within the distal tubular member 58, such as but not limited to a liner that defines an annular fluid pathway extending distally from the fluid pump.

Figure 3:
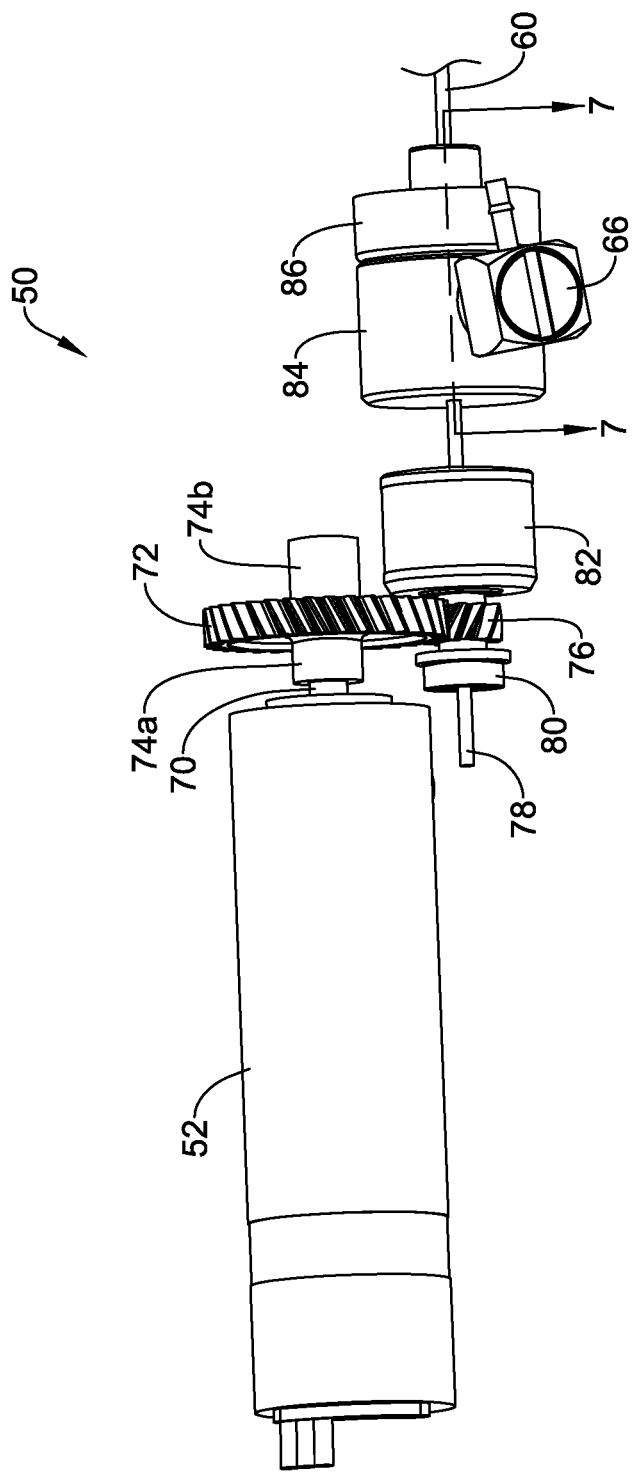
FIG. 3 is a perspective view of a portion of the illustrative drive mechanism of FIG. 2.

FIG. 3 is a perspective view of the illustrative drive mechanism 50 with the housing 54 removed to illustrate internal components. As can be seen, the electric drive motor 52 includes an output shaft 70 that is operably coupled with a drive gear 72. The drive gear 72 includes a bearing surface 74a and a bearing surface 74b that are rotatably supported by the drive gear housing 62 (FIG. 2). The drive gear 72 engages a driven gear 76 that is coupled to a pinion tube 78 that is itself non-rotatably coupled to the drive member 60. A first bearing 80 is visible just proximal of the driven gear 76. The drive gear 72 and the driven gear 76 may be formed of any suitable material. For example, the drive gear 72 may be formed of a polymeric material such as but not limited to polyetheretherketone (PEEK). Other exemplary polymers include but are not limited to polyamideamides, polyetherimide and polyalkyletherketones (PAEK). Alternatively, the drive gear 72 may be formed of a metallic material. The driven gear 76 may be formed of a metallic material such as but not limited to aluminum. Other exemplary metals include but are not limited to brass, titanium and magnesium. The driven gear 76 may also be formed of a polymer such as those described with respect to the drive gear. The drive gear 72 and the driven gear 76 may be configured to provide a drive ratio between the drive gear 72 and the driven gear 76 that ranges from about 2:1 to about 5:1. That is, for each complete revolution of the drive gear 72, the driven gear 76 may go through about 2 to about 5 complete revolutions. In a particular example, the drive ratio may be about 3.5:1. In some cases, the drive mechanism 50 may be configured to provide a rotation speed, measured at the atherectomy burr or cutting member 20, that is up to at least about 200,000 revolutions per minute (rpm). In some cases, the drive mechanism 50 may be configured to provide a rotation speed, measured at the atherectomy burr or cutting member 20, that is up to about 250,000 rpm or even higher. A bearing housing 82 is shown just distal of the driven gear 76 and houses additional components as will be referenced with respect to FIG. 4). The drive member 60 extends through a shaft seal member 84, which will be described in greater detail with respect to FIGS. 5 and 6. A plug member 86 sits just distal of the shaft seal member 84 and serves to provide a fluid tight seal.

Figure 4:
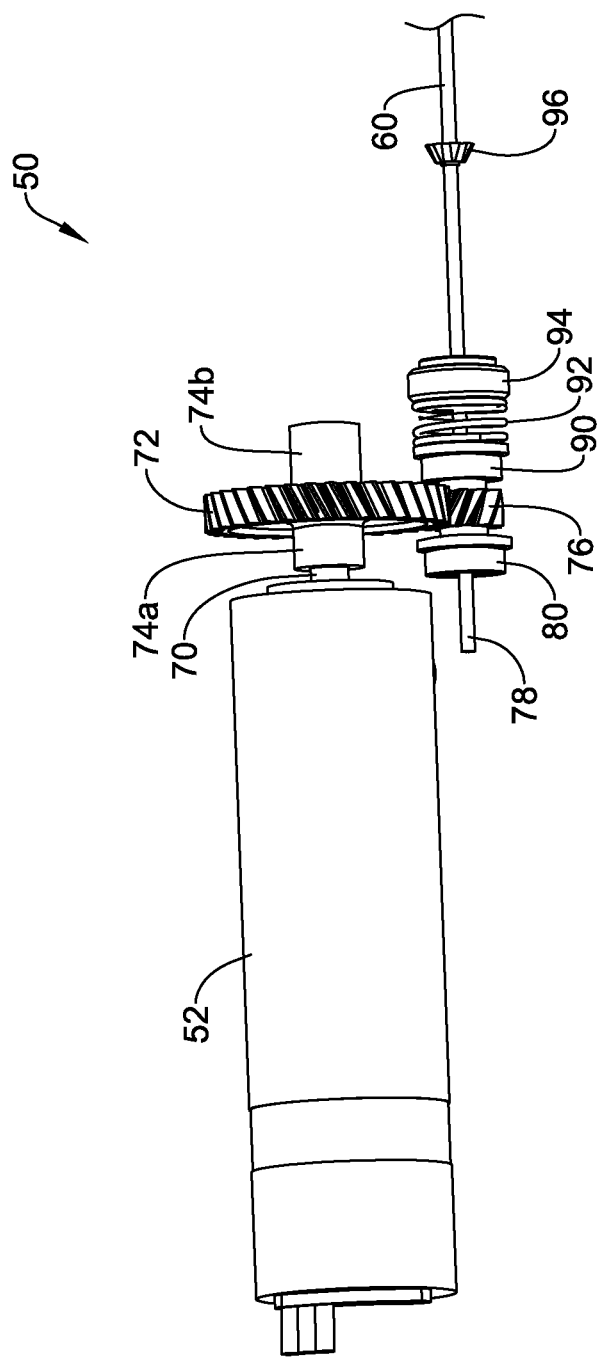
FIG. 4 is a perspective view of a portion of the illustrative drive mechanism of FIG. 2.

In FIG. 4, the bearing housing 82, the shaft seal member 84 and the plug member 86 have been removed to illustrate internal components. As can be seen, the driven gear 76 is positioned between the first bearing 80 and a second bearing 90. A spring 92, which is positioned at least in part via a spring retainer 94, helps to keep the driven gear 76 positioned relative to the drive gear 72 by providing a thrust load to keep the driven gear 76 against the first bearing 80. In some cases, this is a design feature that aids in manufacturing by reducing the tolerance required to keep the driven gear 76 correctly thrust loaded between the first bearing 80 and the second bearing 90. An impeller 96 is secured to the pinion tube 78 (and hence secured to rotate with the drive member 60). The impeller 96 cooperates with the shaft seal member 84 to form a fluid pump that is driven by the electric drive motor 52.

Figure 5:
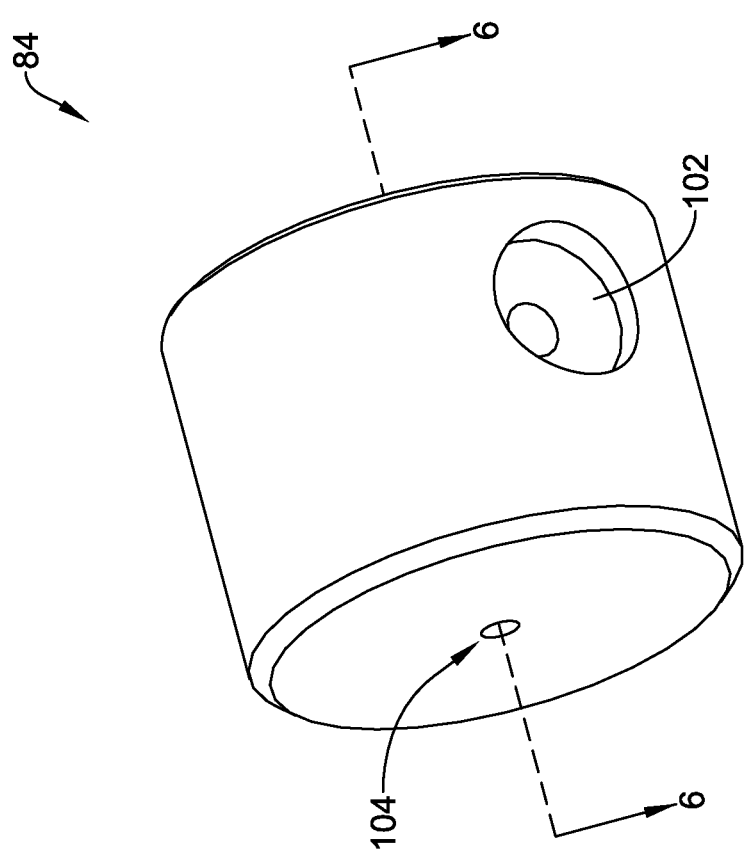
FIG. 5 is a perspective view of an illustrative shaft seal member forming a portion of the illustrative drive mechanism of FIG. 2.
Figure 6:
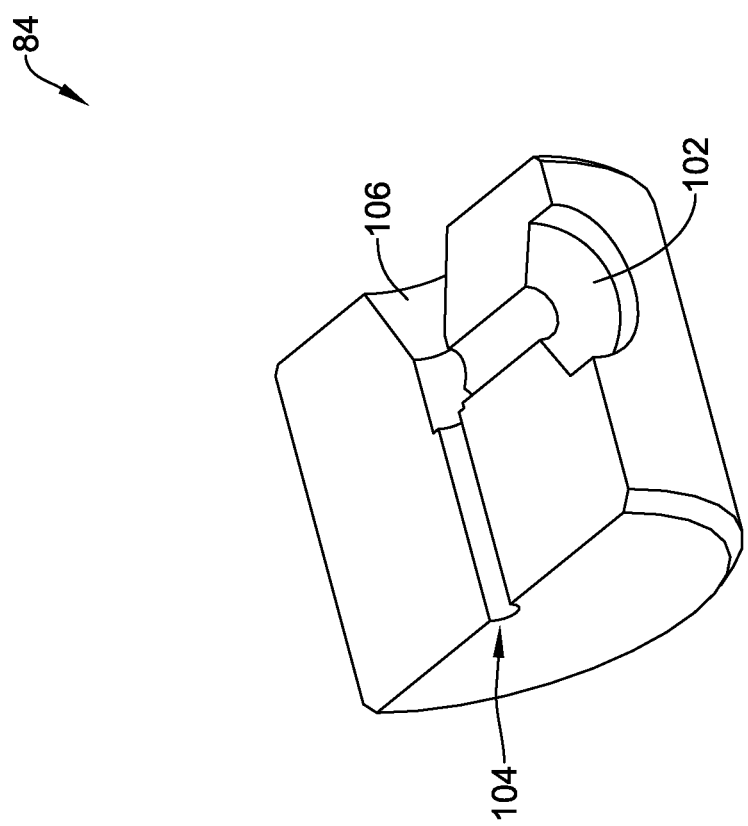
FIG. 6 is a cross-sectional view of the illustrative shaft seal member of FIG. 5, taken along the 6-6 line of FIG. 5.

FIG. 5 is a perspective view of the shaft seal member 84 and FIG. 6 is a cross-sectional view of the shaft seal member 84, taken along line 6-6 of FIG. 5. An aperture 102 may be considered as being configured to accommodate the fitting 66. An aperture 104, which may be considered as accommodating the drive member 60 and attached pinion tube 78, extends through the shaft seal member 84 and is in fluid communication with the aperture 102. The aperture 104 widens into a frustoconical portion 106. It will be appreciated that when the shaft seal member 84 is disposed in position within the drive mechanism 50, the impeller 96 (FIG. 4) will be disposed within the frustoconical portion 106. Rotation of the impeller 96 relative to the frustoconical portion 106 will cause fluid to be pressurized. In some cases, rotation of the impeller 96 may provide a fluid pressure that is in a range of about 10 pounds per square inch (psi) to about 100 psi. In some cases, the fluid pressure may be at least about 50 psi. In some instances, a fluid pressure of up to about 200 psi, may be achieved.

Figure 7:
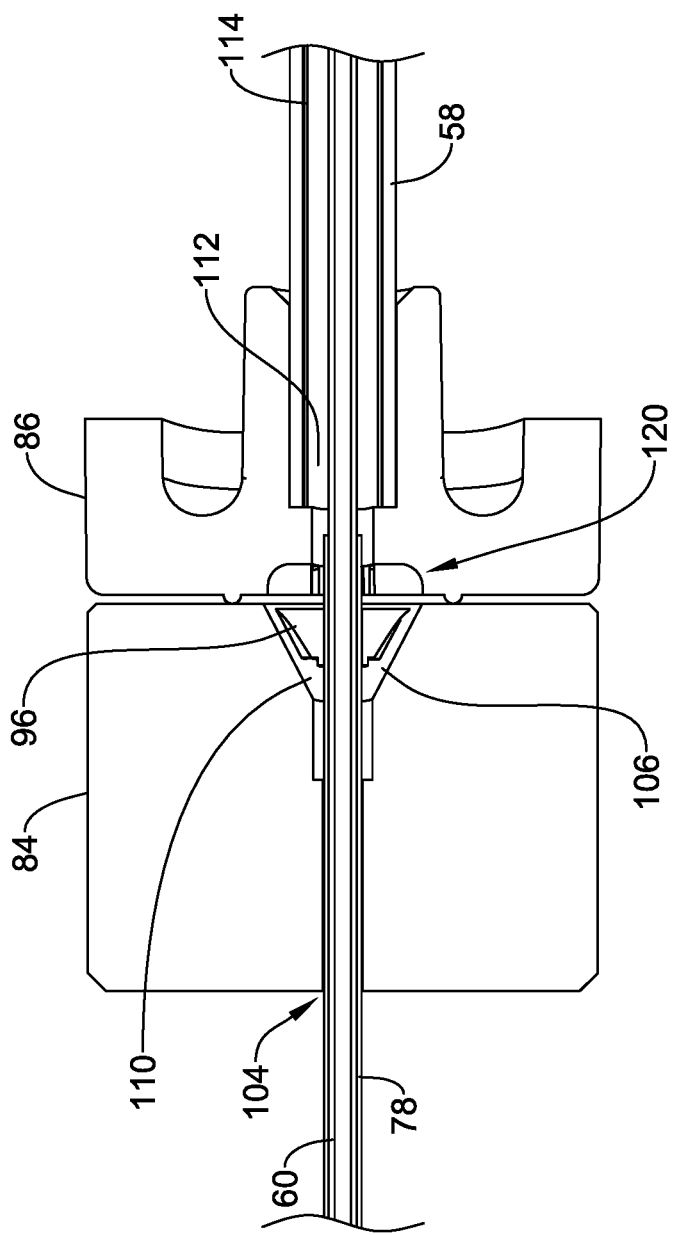
FIG. 7 is a cross-sectional view of a portion of the illustrative drive mechanism of FIG. 3, taken along the 7-7 line of FIG. 3.
Figure 8:
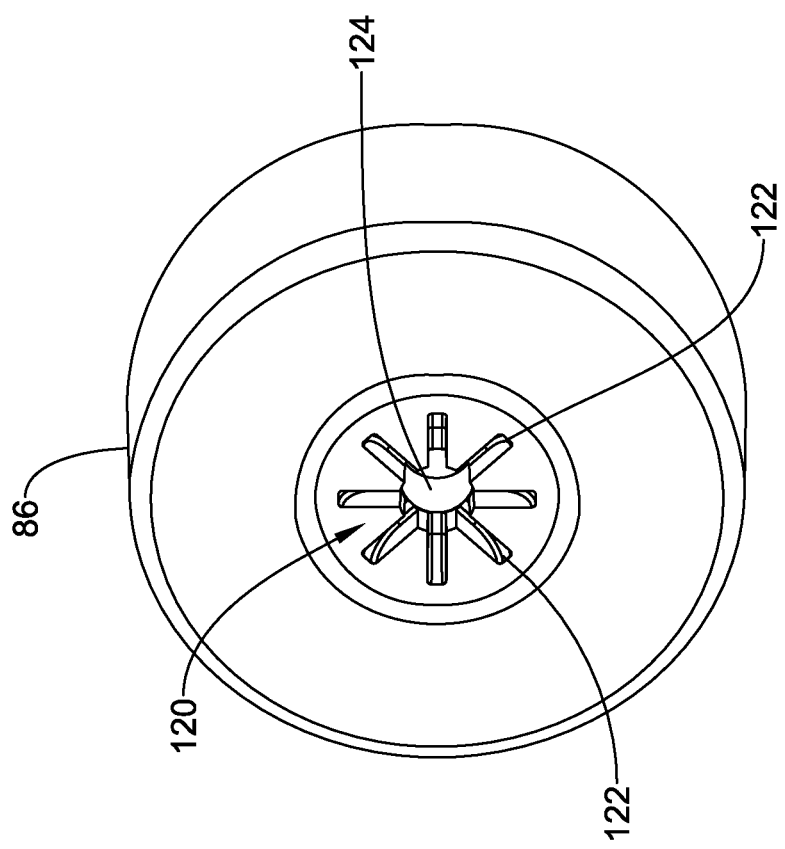
FIG. 8 is a perspective view of a plug member forming a portion of the illustrative drive mechanism of FIG. 2.
Figure 9:
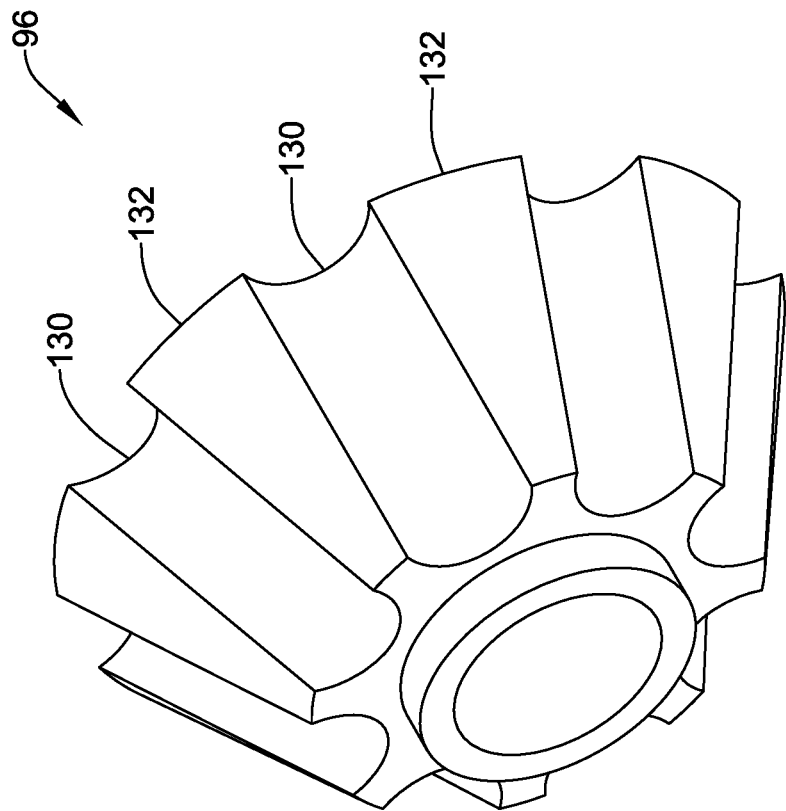
FIG. 9 is a perspective view of an illustrative impeller forming a portion of the illustrative drive mechanism of FIG. 2.

FIG. 7 is a cross-sectional view showing the impeller 96 disposed within the aperture 106. As can be seen, there is a clearance space 110 between the impeller 96 and the walls of the aperture 106. There is also clearance between the plug member 86 and the impeller 96 such that the impeller 96 does not have any physical contact with the shaft seal member 84 and the plug member 86, apart from the pinion tube 78. In some cases, the plug member 86 may be configured to help direct fluid into an annular space 112 that defined between the drive member 60 and an inner surface of the distal tubular member 58 and/or between the drive member 60 and an inner surface of an intermediate tubular member such as a liner 114. In some cases, the plug member 86 may include a region 120 that is configured to cooperate with the impeller 96 in pressurizing fluid and directing the pressurized fluid into the annular space 112. FIG. 8 is a perspective view of the plug member 86. As can be seen, the region 120 includes a plurality of angled or curved passages 122 that are spaced about an aperture 124 that extends through the plug member 86. As can be seen in FIG. 9, the impeller 96 includes alternating flutes 130 and uncut portions 132. It will be appreciated that as the impeller 96 rotates relative to the region 120, the alternating flutes 130 and uncut portions 132 of the impeller 96 will alternatively expose and cover up each of the passages 122.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy system, comprising:
   a handle having a handle housing;
   a drive member extending through the handle housing and operably coupled to an atherectomy burr;
   a drive mechanism disposed within the handle housing and adapted to rotatably engage the drive member, the drive mechanism including:
   an electric drive motor;
   a polymeric drive gear rotatably engaged with the electric drive motor; and
   a metallic driven gear coupled with the drive member and engaged with the polymeric drive gear such that rotation of the metallic driven gear causes rotation of the drive member;
   wherein the drive mechanism is configured to enable a rotation speed of the atherectomy burr of up to at least about 200,000 revolutions per minute (rpm).

2. The atherectomy system of claim 1, wherein the drive mechanism is configured to enable a rotation speed of the atherectomy burr of up to about 250,000 rpm.

3. The atherectomy system of claim 1, wherein the drive gear and the driven gear are configured such that the driven gear goes through about 2 to about 5 revolutions per revolution of the drive gear.

4. The atherectomy system of claim 1, wherein the drive member is configured to accommodate a guidewire extending through the drive member.

5. The atherectomy system of claim 1, further comprising a fluid pump built into the drive mechanism.

6. The atherectomy system of claim 5, wherein the fluid pump comprises an impeller that is secured to the drive member such that the impeller rotates with the drive member, and the impeller is in fluid communication with a source of fluid.

7. The atherectomy system of claim 6, further comprising a shaft seal member that defines a fluid chamber that is in fluid communication with the source of fluid, and the shaft seal member is configured to permit the drive member to extend therethrough with the impeller disposed within the fluid chamber.

8. The atherectomy system of claim 7, further comprising an outer tubular member extending distally of the shaft seal member, such that the drive member extends distally through the outer tubular member, defining an annular space through which fluid may be expelled via the impeller.

9. The atherectomy system of claim 1, wherein the polymeric drive gear comprises a polyetheretherketone (PEEK) drive gear and the metallic driven gear comprises an aluminum driven gear.

10. An atherectomy system, comprising:
a handle having a handle housing;
a drive member extending through the handle housing and operably coupled to an atherectomy burr;
an electric drive motor;
a drive train operably coupling the electric drive motor to the drive member, the drive train comprising:
 a polymeric drive gear that is rotatably engaged with the electric drive motor; and
 a metallic driven gear that is coupled with the drive member and is engaged with the polymeric drive gear such that rotation of the metallic driven gear causes rotation of the drive member; and
a fluid pump driven by the electric drive motor.

11. The atherectomy system of claim 10, wherein the fluid pump comprises an impeller that is secured to the drive member such that the impeller rotates with the drive member, and the impeller is in fluid communication with a source of fluid.

12. The atherectomy system of claim 11, further comprising a fluid chamber that is in fluid communication with the source of fluid, with the impeller disposed within the fluid chamber.

13. The atherectomy system of claim 10, wherein the drive train is configured to enable a rotation speed of the atherectomy burr of up to at least about 200,000 revolutions per minute (rpm).

14. The atherectomy system of claim 10, wherein the fluid pump provides a fluid pressure of about 10 pounds per square inch (psi) to about 100 psi.

15. The atherectomy system of claim 10, wherein the polymeric drive gear comprises a polyetheretherketone (PEEK) drive gear and the metallic driven gear comprises an aluminum driven gear.

16. An atherectomy system, comprising:
a handle having a handle housing;
a drive member extending through the handle housing and operably coupled to an atherectomy burr;
a drive mechanism disposed within the handle housing and adapted to rotatably engage the drive member, the drive mechanism including:
 an electric drive motor;
 a polyetheretherketone (PEEK) drive gear rotatably engaged with the electric drive motor; and
 an aluminum driven gear coupled with the drive member and engaged with the PEEK drive gear such that rotation of the aluminum driven gear causes rotation of the drive member; and
a fluid pump driven by the drive mechanism;
wherein the drive mechanism is configured to enable a rotation speed of the atherectomy burr of up to at least about 200,000 revolutions per minute (rpm).

17. The atherectomy system of claim 16, wherein the fluid pump comprises an impeller that is secured to the drive member such that the impeller rotates with the drive member, and the impeller is in fluid communication with a source of fluid.

18. The atherectomy system of claim 17, further comprising a fluid chamber that is in fluid communication with the source of fluid, with the impeller disposed within the fluid chamber.

* * * * *